United States Patent
Korn

(10) Patent No.: US 7,132,645 B2
(45) Date of Patent: Nov. 7, 2006

(54) SYSTEM AND METHOD FOR ASSESSING CATHETER CONNECTION USING RETURN LOSS

(75) Inventor: Jeffrey A. Korn, Lexington, MA (US)

(73) Assignee: InfraReDx, Inc., Burlington, MA (US)

( * ) Notice: Subject to any disclaimer, the term of this patent is extended or adjusted under 35 U.S.C. 154(b) by 220 days.

(21) Appl. No.: 10/384,342

(22) Filed: Mar. 7, 2003

(65) Prior Publication Data

US 2004/0173733 A1   Sep. 9, 2004

(51) Int. Cl.
  *G01J 1/04* (2006.01)
  *G01N 21/00* (2006.01)
(52) U.S. Cl. .................. 250/227.11; 356/73.1
(58) Field of Classification Search ........... 250/227.11, 250/227.14, 227.15; 356/73.1; 600/103, 600/112; 385/13
See application file for complete search history.

(56) References Cited

U.S. PATENT DOCUMENTS

| | | | |
|---|---|---|---|
| 4,543,477 A * | 9/1985 | Doi et al. .............. | 250/227.11 |
| 4,741,616 A | 5/1988 | So et al. | |
| 4,899,045 A | 2/1990 | Kramer | |
| 5,625,450 A | 4/1997 | Ikeno | |
| 6,009,220 A | 12/1999 | Chan et al. | |
| 6,102,917 A * | 8/2000 | Maitland et al. ........... | 606/108 |
| 6,711,426 B1 * | 3/2004 | Benaron et al. ........... | 600/342 |
| 6,784,983 B1 * | 8/2004 | Bjerkan et al. ............ | 356/73.1 |

FOREIGN PATENT DOCUMENTS

| | | |
|---|---|---|
| EP | 0 560 426 A | 9/1993 |
| EP | 1 186 274 | 3/2002 |
| WO | WO/ 98/41836 | 9/1998 |
| WO | WO 02/069797 | 9/2002 |

OTHER PUBLICATIONS

International Preliminary Report on Patentability from International Patent Application PCT/US2002/006691, filed Mar. 5, 2004.

* cited by examiner

*Primary Examiner*—Thanh X. Luu
(74) *Attorney, Agent, or Firm*—Houston Eliseeva LLP

(57) ABSTRACT

A system for assessing the quality of the optical connection between a catheter and a console is described that avoids the necessity of a calibration port, although one can still be provided if desired. It operates by monitoring the level of light returning from the catheter head and specifically the degree to which this returning light is attenuated. Reflections will arise at the catheter head's optical window due to the discontinuity between the refractive index of the window and that of air or other medium into which the head is inserted. Since the refractive index of the optical window is known and with the head in a known medium such as air, the level of reflection is known. This enables a controller in the console to calculate the round trip loss and thus monitor the loss in the catheter-console interface. Moreover, since round-trip loss is measured, the accuracy is improved by a factor of two over calibration port systems that only measure loss in a single pass arrangement. One embodiment provides for the assessment of a multi-piece catheter using multiple wavelengths.

36 Claims, 4 Drawing Sheets

SYSTEM AND METHOD FOR ASSESSING CATHETER CONNECTION USING RETURN LOSS

BACKGROUND OF THE INVENTION

Catheter-based optical systems are applicable to a number of diagnostic and therapeutic medical applications. Optical coherence tomography is used to provide spatial resolution, enabling the imaging of internal structures. Spectroscopy is used to characterize the composition of structures, enabling the diagnosis of medical conditions, by differentiating between cancerous, dysplastic, and normal tissue structures. Ablation systems are used to remove or destroy structures within the body to address various diseases, such as tachycardias, tumors, and coronary artery disease, for example.

For example, in one specific spectroscopic application, a tunable laser source is used to scan a spectral band of interest, such as a scan band in the near infrared or 850 nanometers (nm) to 1–2 micrometers (μm), for example. The generated light is used to illuminate tissue in a target area in vivo using the catheter. Diffusely reflected light resulting from the illumination is then collected and transmitted to a detector and a spectral response resolved. The response is used to assess the state of the tissue.

One specific example is the diagnosis of atherosclerosis, and the identification of atherosclerotic lesions or plaques. This is an arterial disorder involving the intimae of medium- or large-sized arteries, including the aortic, carotid, coronary, and cerebral arteries. Efforts are being made to spectroscopically analyze blood vessel walls and characterize any atherosclerotic lesions.

These catheter-based optical systems typically comprise a console, such as hand-held, rack mountable, or floor unit. A fiber optical probe or catheter connects to the console. The catheter is used to deliver optical energy to and/or receive energy from regions of interest on or in the patient.

The catheter is usually plugged into an optical port of the console. Many times the catheter is disposable, being limited to one time usage. Therefore, after usage, it must be disconnected and disposed of. Even if the catheter is not disposable, it must be disconnected for sterilization between usages.

The quality of the optical connection between the console and the catheter is relevant to the optical performance of the machine. A damaged or dirty interface minimally can degrade the power of the optical signal transmitted to the patient and/or received from the patient. In spectroscopic applications, for example, a dirty interface can also lead to spurious results.

One method for assessing the quality of the optical interface is to additionally provide the console with a calibration port. The end of the probe is inserted into the calibration port and the optical system energized. This allows the optical system to be tested at the point of delivery.

SUMMARY OF THE INVENTION

The problem with the calibration port solution is that it contributes to the cost of machine. Moreover, in real-world applications, it may not actually improve the operator's ability to assess the level at which the system is operating since a new variable is now introduced, which is the cleanliness of the calibration port.

The present invention concerns a system for assessing the quality of the optical connection between a catheter and a console. It avoids the necessity of a calibration port, although one can still be provided, if desired. The invention operates by monitoring the level of light returning from the catheter head and specifically the degree to which this returning light is attenuated from the input signal.

Generally, reflections will arise at the catheter head's optical window due to the discontinuity between the refractive index of the window and that of air or other medium, into which the head is inserted. Since the refractive index of the optical window is known and with the head in a known medium such as air, the level of reflection is known. This enables a controller in the console to calculate the round trip loss and thus monitor the loss in the catheter-console interface. Moreover, since round-trip loss is typically measured, the accuracy is improved by a factor two over calibration port systems that only measure loss in a single pass arrangement.

In other embodiments, the known reflectors, such as dichroic filters, are inserted into the optical train of the catheter to provide the return signal.

In general, according to one aspect, the invention features a method for assessing an optical connection between a console and a catheter. The method comprises generating a test signal in the console that is coupled into the catheter via a connector. A level of the test signal returning to the console from the catheter via the connector is then measured. A state of the connector is then assessed in response to the level of the returning test signal.

In one implementation, the step of generating the test signal comprises modulating the test signal. The returning signal can then be determined using lock-in detection to improve the system's tolerance to stray light.

In the preferred embodiment, a level of the test signal is detected prior to being coupled into the catheter. This allows the system to more accurately measure the return loss, since the level of the input signal is now known. The transmission through the connector can be determined in response to the level of the returning test signal. The operator is typically signaled to clean and/or reconnect the catheter to the console if the level of the returning test signal is too low, for example.

In general, according to another aspect, the invention features a method or system for assessing optical interfaces between a console and a catheter head. Here, multiple optical interfaces are provided with separate optical signatures and then test signals generated in the console that are coupled into the catheter via the interface. The test signals are defined based on the signatures. For example, in one embodiment, the signatures are wavelength dependent reflectivities and the wavelength of the test signals are set so that they are returned by the reflectivities, such that one test signal is returned by each signature. The levels of the test signals returning to the console from the catheter due to the optical signatures are measured and a state of the interfaces assessed in response to the levels of the returning test signals.

In general, according to still another aspect, the invention features a system for assessing a quality of a catheter connection for an optical catheter device. This device preferably includes: 1) a console with a catheter connector; and 2) a catheter with a console connector and an output window. The system comprises an optical source in the console that generates a test signal that is coupled into the catheter via the console connector and the catheter connector and a returning signal detector in the console for detecting a level of the test signal returning to the console via the catheter. A controller is then used to assess the quality of catheter connection in response to the returning signal detector.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figures 1A, 1B:
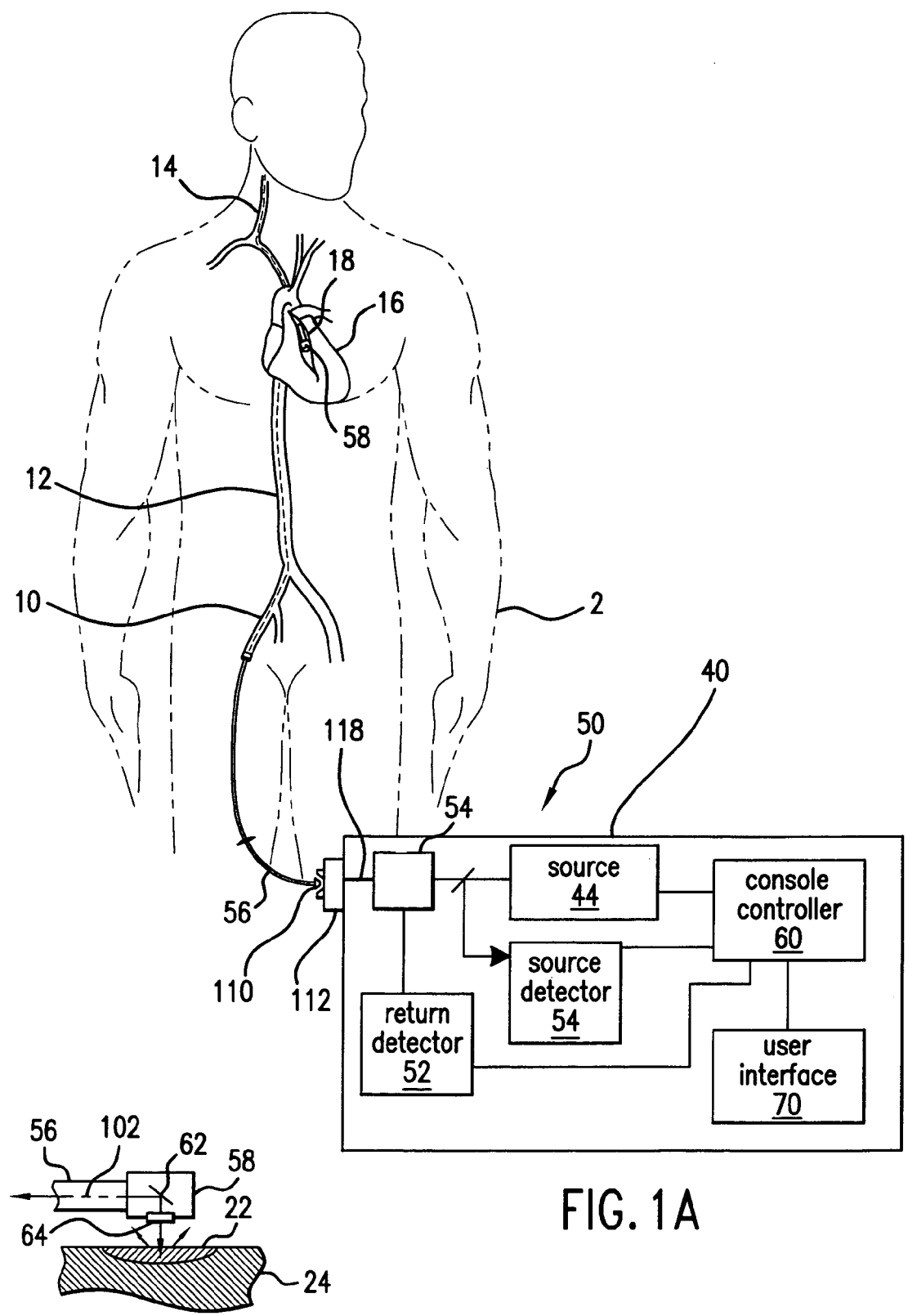
FIG. 1A is a schematic block diagram illustrating a catheter-based medical optical system to which the inventive system for assessing a quality of a catheter connection is applicable.
FIG. 1B is a cross-sectional view of the catheter head positioned adjacent tissue illustrating the operation of the medical system.

FIG. 1A shows a catheter-based medical optical system 50 to which the present invention is applicable.

The specific, illustrated catheter system 50 is used for spectroscopic analysis of the intimae of blood vessels to find atherosclerotic lesions or plaque. But, this system 50 is described only as an example, the present invention being applicable not only to this application, but other medical applications in which a catheter is connected to a console. Thus, it is further applicable to imaging systems and treatment systems such as ablation systems, for example.

In any event, turning to the current implementation, the catheter system 50 generally comprises a console 40 and catheter 56 that includes an optical fiber or optical fiber bundle. The catheter 56 is typically inserted into the patient 2. This can be accomplished via a peripheral vessel, such as the femoral artery 10, when analyzing blood vessels. The catheter head 58 is then moved to a desired target area, such as a coronary artery 18 of the heart 16 or the carotid artery 14. In the example, this is achieved by moving the catheter head 58 up through the aorta 12.

In other applications, the catheter is moved through the body 2 other than through blood vessels such as in endoscopes.

The console 40 comprises a source 44. This can be a narrow band or broad band source. In spectroscopic applications, it is usually a broad band source or a tunable narrow band source to cover the scan band of interest. In other implementations, multiple sources are included.

According to one preferred embodiment of the invention, a source detector 54 is provided to detect the output power of the source 44 to provide for feedback control via the console controller 60. Thus, the output power and possibly wavelength of the source 44 is typically determined by the console controller 60 prior being coupled into the catheter 56 via a coupler 54, such as a circulator.

The optical radiation from the source 44 is transmitted in a waveguide 118 that terminates in a catheter connector 112 of the console 40. The catheter connector 112 of the console 40 mates or engages with a console connector 110 of the catheter 56.

This arrangement of the catheter connector 112 and console connector 110 facilitates the operation of the optical system 50 in the clinical environment. The catheter 56 is thus able to be disconnected after usage and sterilized or disposed of, in a single use system.

A return detector 52 is also connected to the coupler 54. It is used to detect the light returning from the catheter 56. For the present invention, it is used to measure the level of the returning light from the catheter head, which was generated by the source 44. During normal operation, the return detector 52 is also used, in some implementations. For example, in spectroscopy applications, the return detector also functions to resolve the spectrum of the returning light.

During operation, when at the desired site, radiation such as near infrared (NIR) radiation is generated by the source 44 in the current embodiment. It is coupled into the optical fiber of the catheter 56 to be transmitted to the catheter head 58.

In more detail, with reference to FIG. 1B, the radiation or optical signal 102 from the optical fiber of the catheter 56 is directed by a fold mirror 62, for example, to exit from the catheter head 58 via an output or catheter window 64 and impinge on the target area 22 of the body such as an artery wall 24. In the current example, the catheter head 58 then collects reflected and scattered radiation from the target area 22 through the same window 64.

In other embodiments, the catheter head either just collects radiation during operation or just emits radiation during operation.

Figure 2:
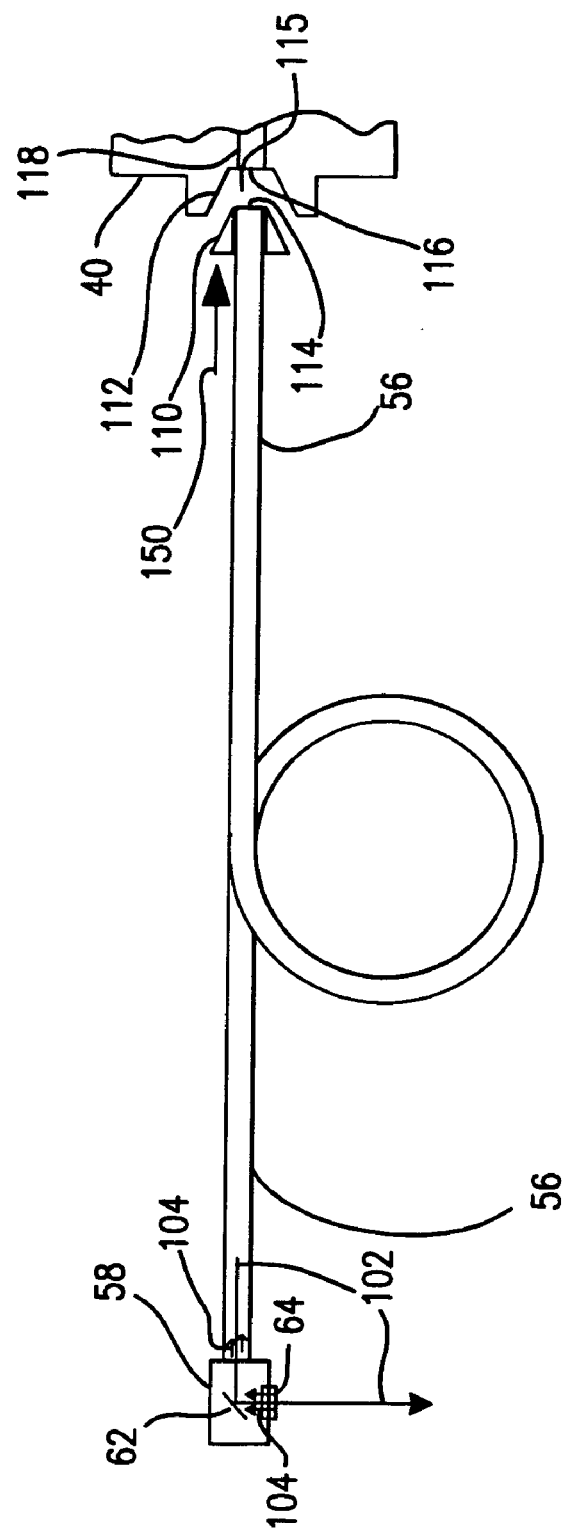
FIG. 2 is a schematic diagram of the catheter and its connection to the console according to the invention.

FIG. 2 illustrates how the controller 60 assesses the optical connection or interface 115 between the catheter 56 and the console 40 according to the principles of the present invention.

Light or radiation from the source 44 is transmitted in the console 40 via the guide 118 to the catheter connector 112. It is conveyed into the optical interface 115 between the exit facet 116 of console waveguide 118 and the entrance facet 114 of the catheter 56.

Traveling through this interface 115, the light will experience loss due to any dirt or other scattering or absorbance here. Another problem can arise from a failure to fully seat the console connector 110 into the catheter connector 112 by the operator by inserting the catheter 56 in the direction of arrow 150. This will reduce the transmission through the interface 115.

The generated light 102 that is coupled into the catheter 56 travels through the catheter waveguide(s) to the catheter head 58 and specifically window 64.

For the calibration protocol, the operator is instructed to place the catheter head 58 in a know medium such as air. As a result the known refractive index mismatch between the medium, such as air, and the material of the catheter window 64 will produce a known reflection at the interface. This will cause a portion of the generated light 102 to be reflected 104 to travel back down the catheter 56.

The reflected light 104 will again pass through the interface 115 experiencing any loss in the interface and be detected by the return detector 52. By monitoring the response of the return detector 52, the console controller 60 is able to assess the optical connection between the catheter 56 and the console 40.

For example, the reflective index mismatch between a non-antireflection coated silica window 64 and air will produced a reflectivity at the catheter head of $R_{end}$=0.0359.

The transmission through the interface 115 is then:

$$T_{interface} = \sqrt{(RL/R_{end})}$$

where RL is the measured return loss or difference between the level of generated light 102 measured by the source detector 54 and the level of light measured by the return detector 52. This assumes that other losses, such as in the coupler 54, are negligible.

Available power is also be calculated as follows:

$$P_{available} = T_{interface}(1-R_{end})$$

The controller 60 is then able to determine if the interface transmission is acceptable and appropriately signal the operator via the user interface 70.

Figure 3:
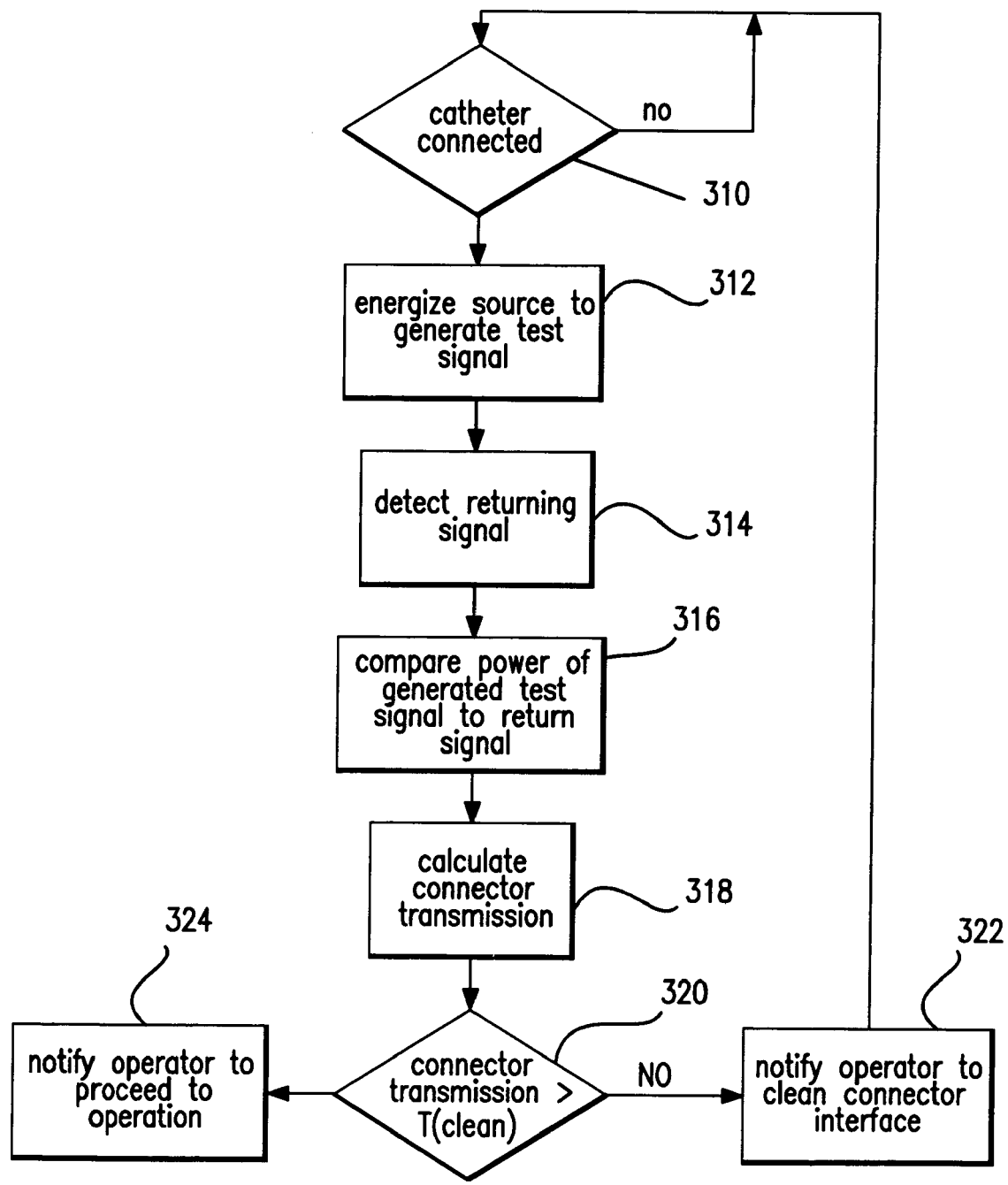
FIG. 3 is a flow diagram illustrating the operation of the system for assessing the catheter connection according to the present invention.

FIG. 3 is a flow diagram illustrating method for assessing an optical connection between a console 40 and a catheter 56 according to the principles of the present invention.

In step 310, the controller 60 waits for the connection of the catheter 56 and/or a test request from the operator via interface 70. When received, it then starts the process of confirming whether the interface 115 between the catheter 56 and the console 40 is operating properly.

A test signal is generated in the console 40 by the source 44 that is coupled into the catheter 56 via the interface 115 including the catheter connector 112 and the console connector 110, in step 312.

In one implementation, the test signal is a modulated signal. This allows the controller 60 to apply lock-in detection or matched filtering. Thus, the controller 60 is able to detect only the returning test signal, even in the presence of stray light from other sources, which are coupled into the catheter head 58 and/or the interface 115, in step 314.

In step 316, the level of the returning test signal 104 measured by the return detector 52 is compared to the detected level of the test signal 102 as measured by the source detector 54. This is performed by the controller 60. From the available information, the return loss is calculated by the controller 60. The return loss is the ratio of the input test signal to the returning test signal.

In the current embodiment, the controller 60 determines a transmission through the interface 115 and specifically the connectors 110, 112. If the transmission through the interface 115 is determined to be less than a threshold ($T_{clean}$), in step 320, the operator is preferably signaled to clean the interface in step 322 and perform a retest. In contrast, if the transmission is adequate, is operator is notified to proceed in step 324.

Figure 4:
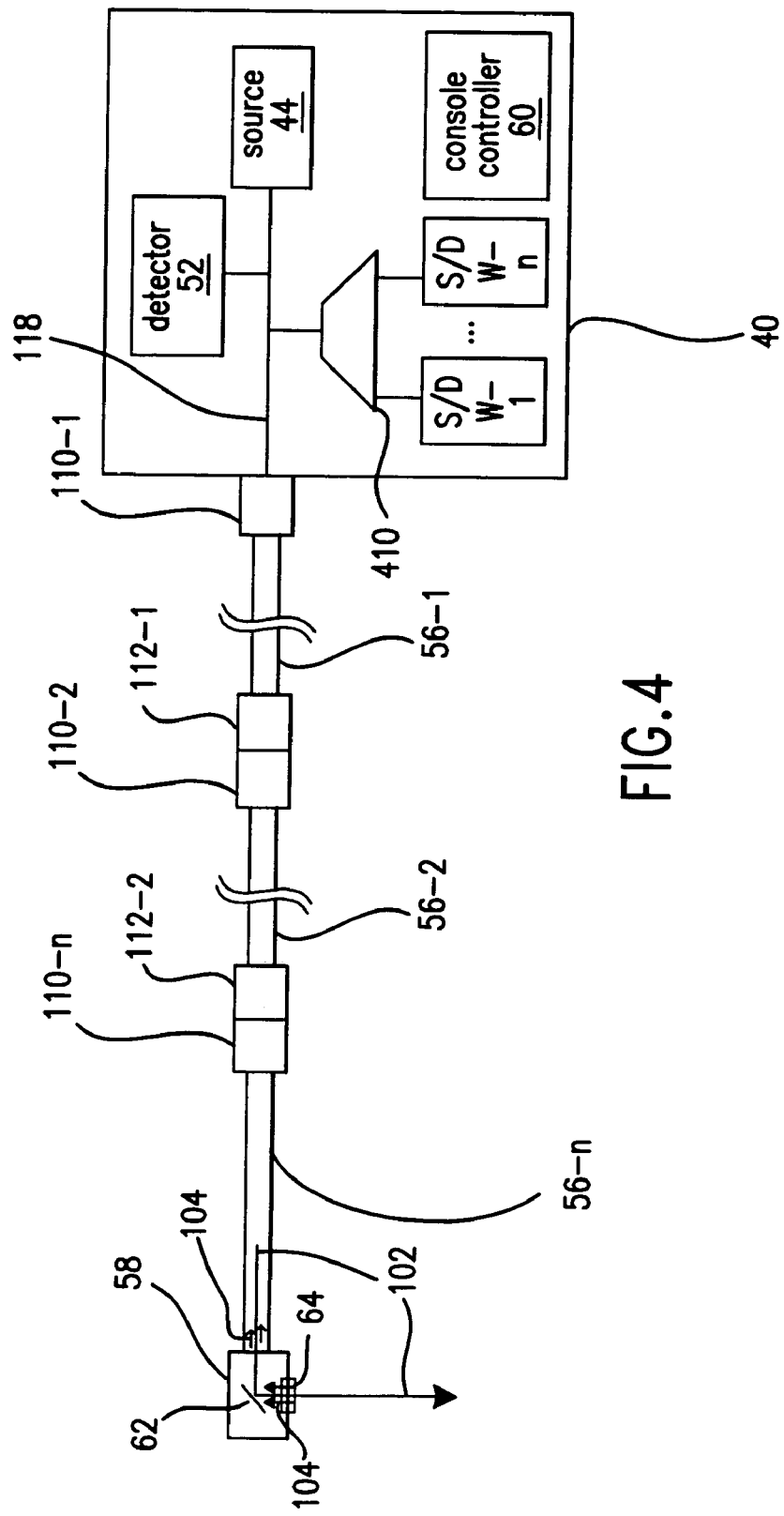
FIG. 4 is schematic diagram of the catheter and the console of the catheter-based medical optical system according another embodiment of the invention.

As illustrated in FIG. 4, the present invention is applicable also to systems having multi-piece catheter systems or multiple elements in the optical path between the catheter head 58 or final output port and the source/detector 44, 52 of the console 40.

Generally in this alternative embodiment, multiple connections between multiple, series connected elements are assessed by providing multiple optical sources at a set of wavelengths or a single source that is tunable or able to generate light at those wavelengths. The connections are then each provided with a unique optical signature that is accessible by those wavelengths.

In more detail according to one implementation, the console 40 has a source 44 and return detector 52 as described previously. It further has a wavelength multiplexer/demultiplexer 410 such as an arrayed waveguide grating. This multiplexer/demultiplexer functions to combine the light generated by a system of test sources and a system of corresponding test detectors. Specifically, the multiplexer/demultiplexer functions to combine test signals from multiple source/detector pairs S/D. Each one of these source/detectors S/D generates a test signal at a predetermined wavelength w-1 ... w-n. These signals are combined onto waveguide 118 and transmitted from the console 40.

In the illustrated example, multiple elements 56-1 to 56-n are present on the optical path to the output port of the catheter head 58. Elements 56-1 and 56-2 each have corresponding input connectors 110 and output connectors 112. The final element 56-n has only an input connector 110-n. Each of the input connectors 110-1 to 110-n, in the preferred embodiment, is optically coated, using thin film dielectric, dichroic coatings to create the optical signature. Specifically they are highly reflective (HR) at some of the wavelengths w-1 to w-n and anti-reflection (AR) coated for the other wavelengths.

For example in one scheme, input connector 110-1 is coated to be highly reflecting to wavelength w-1, but AR coated relative to wavelengths w-2 to w-n. Similarly, input connector 110-2 for element 56-2 is highly reflecting to wavelength w-2, but AR coated relative to wavelengths w-3 to w-n. Finally, in the three-element example illustrated, input connector 110-n for element 56-n is highly reflecting to wavelength w-n.

Thus, source detector pair S/D w-1 is used to determine the transmission to the input connector 110-1 since wavelength w-1 is reflected at connector 110-1, enabling determination of the return loss using the detector in S/D w-1. Source/detector S/D w-2 is used to determine the transmission to input connector 110-2, since wavelength w-2 is transmitted through connector 110-1 and reflected by connector 110-2. Source/detector S/D w-2 is thus able to determine the return loss to connector 110-2. Finally, source/detector S/D w-n is used to determine the transmission to input connector 110-n since wavelength w-n is transmitted through connectors 110-1 and 110-2 and reflected by connector 110-n. Source/detector S/D w-n is thus able to determine the return loss to connector 110-n.

With cumulative return loss information available to each input connector, the transmission through each optical interface between each input connector and output connector pair is determined by the controller 60.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for using a spectroscopic catheter system having an optical interface between a console and a catheter, the method comprising:

generating a test signal in the console that is coupled into the catheter via the interface;

detecting a level of the test signal returning to the console from the catheter via the interface;

assessing a state of the interface in response to the level of the returning test signal; and generating a spectroscopy signal in the console that is coupled into the catheter through the optical interface and resolving a spectrum of light returning from the catheter.

2. A method as claimed in claim 1, wherein the step of generating the test signal comprises modulating the test signal.

3. A method as claimed in claim 2, wherein the step of detecting the returning signal comprises lock-in detecting the returning test signal.

4. A method as claimed in claim 1, further comprising detecting a level of the test signal prior to being coupled into the catheter.

5. A method as claimed in claim 4, further comprising comparing a level of the returning test signal to the detected level of the test signal prior to being coupled into the catheter.

6. A method as claimed in claim 1, further comprising determining a transmission through the interface in response to the level of the returning test signal.

7. A method as claimed in claim 1, further comprising signaling an operator to clean and/or reconnect the catheter to the console in response to the level of the returning test signal.

8. A method as claimed in claim 1 wherein the catheter comprises multiple pieces, the method further comprising:
   testing the multiple pieces by providing each of the pieces with separate optical signatures; and
   assessing the optical signatures using multiple test signals.

9. A method as claimed in claim 1, wherein the test signal is reflected by an exit window of the catheter.

10. A method as claimed in claim 1, wherein the test signal is reflected by a reflective coating in the catheter.

11. A method as claimed in claim 10, wherein the reflective coating is reflective at a wavelength of the test signal and transmissive at other wavelengths.

12. A method as claimed in claim 1, wherein the test signal is reflected by a reflective element in the catheter.

13. A method as claimed in claim 12, wherein the reflective element is reflective at a wavelength of the test signal and transmissive at other wavelengths.

14. A method for assessing optical interfaces between a console and a catheter head of a catheter, the method comprising:
   providing the optical interfaces with separate optical signatures;
   generating test signals in the console that are coupled into the catheter;
   detecting levels of the test signals returning to the console from the catheter due to the optical signatures; and
   assessing a state of the interfaces in response to the levels of the returning test signals.

15. A spectroscopy system that assesses a quality of a catheter connection for an optical catheter device including a console with a catheter connector and a catheter with a console connector and an output window, the system comprising:
   an optical source system in the console that generates a test signal that is coupled into the catheter via the console connector and the catheter connector, and that generates a spectroscopy signal that is coupled into the catheter via the console connector and the catheter connector;
   a returning signal detector system in the console for detecting a level of the test signal and the spectroscopy signal returning to the console via the console connector and the catheter connector; and
   a controller for assessing the quality of the catheter connection in response to the returning signal detector system and resolving a spectral response based on the spectroscopy signal.

16. A system as claimed in claim 15, wherein the optical source system generates a modulated test signal.

17. A system as claimed in claim 16, wherein the returning signal detector system lock-in detects the returning test signal.

18. A system as claimed in claim 15, further comprising a source detector for detecting a level of the test signal prior to being coupled into the catheter.

19. A system as claimed in claim 18, wherein the controller compares a level of the returning test signal to the detected level of the test signal prior to being coupled into the catheter.

20. A system as claimed in claim 15, wherein the controller determines a transmission through the catheter connection in response to the level of the returning test signal.

21. A system as claimed in claim 15, further comprising a user interface, the controller signaling an operator to clean and/or reconnect the catheter to the console in response to the level of the returning test signal via the user interface.

22. A system as claimed in claim 15, wherein the catheter comprises multiple pieces, the pieces having separate optical signatures; the optical source generating multiple test signals to assess the separate optical signatures.

23. A system as claimed in claim 15, wherein the catheter comprises an optical fiber and the test signal and the spectroscopy signal are coupled into the optical fiber via the console connector.

24. A system as claimed in claim 15, wherein the test signal is reflected by an exit window of the catheter.

25. A system as claimed in claim 15, wherein the test signal is reflected by a reflective coating in the catheter.

26. A system as claimed in claim 25, wherein the reflective coating is reflective at a wavelength of the test signal and transmissive at other wavelengths.

27. A system as claimed in claim 15, wherein the test signal is reflected by a reflective element in the catheter.

28. A system as claimed in claim 27, wherein the reflective element is reflective at a wavelength of the test signal and transmissive at other wavelengths.

29. A system for assessing a quality of optical connections between a catheter head and a console, the system comprising:
   an optical source system in the console that generates test signals at different wavelengths that are coupled into the optical connections to the catheter head;
   separate optical signatures corresponding to the different wavelengths for each of the optical connections;
   a returning signal detector system in the console for detecting levels of the test signals returning to the console from each of the optical connections; and
   a controller for assessing the quality of the optical connections in response to the returning signal detector system.

30. A system as claimed in claim 29, wherein the optical signatures are generated by thin film dichroic coatings that are reflective at the different wavelengths.

31. A system for the spectroscopy analysis of blood vessels, the system comprising:
   a console;
   a tunable laser system in the console that generates a tunable signal;

a catheter that is inserted into the blood vessels, the tunable signal being coupled into the catheter via an optical interface, the catheter collecting light from the blood vessels, which is transmitted to the console via the optical interface;

a returning signal detector system in the console for detecting the collected light and portions of the tunable signal that are reflected in the catheter; and a controller for determining a spectral response of the blood vessels from the collected light and for assessing a quality of the optical interface in response to the tunable signal reflected by the catheter.

32. A system as claimed in claim 31, wherein the tunable signal reflected by the catheter is reflected by an exit window of the catheter.

33. A system as claimed in claim 31, wherein the tunable signal reflected by the catheter is reflected by a reflective coating in the catheter.

34. A system as claimed in claim 33, wherein the reflective coating is reflective at a wavelength test signal for the optical interface and transmissive at other wavelengths.

35. A system as claimed in claim 31, wherein the tunable signal reflected by the catheter is reflected by a reflective coating in the catheter.

36. A system as claimed in claim 35, wherein the reflective coating is reflective at a wavelength test signal for the optical interface and transmissive at other wavelengths.

* * * * *